United States Patent [19]

Isojima et al.

[11] Patent Number: 5,348,866

[45] Date of Patent: Sep. 20, 1994

[54] GENES ENCODING PORCINE ZONA PELLUCIDA PROTEIN PZP-4, EXPRESSION THEREOF AND CONTRACEPTIVE VACCINES COMPRISING EXPRESSED (POLY) PEPTIDES

[75] Inventors: Shinzo Isojima, 9-12 Kendani-cho, Nishinomiya-shi, Hyogo-ken; Akiko Akatani, Nishyinomiya; Yuichi Okazaki, Chiba; Masanobu Sugimoto, Shiki, all of Japan

[73] Assignees: Shinzo Isojima, Nishinomiya; Tonen Corporation, Chiyoda, both of Japan

[21] Appl. No.: 855,411

[22] Filed: Mar. 20, 1992

[30] Foreign Application Priority Data

Jan. 10, 1992 [JP] Japan ................................. 4-21818

[51] Int. Cl.$^5$ ................... A61K 37/00; A61K 39/00; C12N 15/12

[52] U.S. Cl. ................................. 435/673; 424/185.1; 424/581; 424/582; 424/811; 435/172.1; 435/172.3; 530/350; 530/853; 536/23.5; 536/23.1

[58] Field of Search ............... 435/69.3; 530/350, 403, 530/806, 412, 395; 424/88

[56] References Cited

U.S. PATENT DOCUMENTS 4,996,297  2/1991  Dunbar ............................. 530/395

FOREIGN PATENT DOCUMENTS

WO89/03399  4/1989  PCT Int'l Appl. .
WO90/15624  12/1990  PCT Int'l Appl. .

OTHER PUBLICATIONS

Liang, Li-Fang. 1990. Oocyte-specific expression of mouse-ZP-2: developmental regulation of the Zona Pellucida genes. Mol. & Cell. Biolog. 10(4): 1507–1515.
Young, R. A. et al. Proc. Natl. Acad. Sci. 80: 1194–1198 (1983).
Sambrook, J et al. Molecular Cloning Cold Spring Harbor Labs (1989) pp. 11.2–11.19.
Jurrien, D. 1990 Contraceptive Vaccine Based on Cloned Zona Pellucida Genes. NTIS order #Pat-Appl-7-364-379.
Moller, Christopher C. et al. 1989 Characterization of a Proteinase That Cleaves Zona Pellucida Glycoprotein ZP2 Following Activation of Mouse Eggs. Dev. Biol. 132:103–112.
Serrano, H. et al Dec. 8–12, 1991 cDNA Library Expressing Ovarian Pig Genes. J. Cell Biology. 115 (3 part 2) 462A.
Bleil, Jeffrey D. 1988. Identification of a $Z^0$ Sperm Receptor in the Mouse Egg Zona Pellucida: Role in Maintenance of Binding of Acrosome-Reacted Sperm to Eggs. Dev. Biol. 128:376–385.
M Koyama, et al., *Biology of Reproduction*, 45:727–735 (1991).
Database WPIL, Week 8831, Derwent Publications, AN 88-215529 (31) of JP-A-63 150 299 (TOA Nenryo Kogyo KK) Jun. 22, 1988 Abstract.
Database WPIL. Week 9033, Derwent Publications, AN90-250685 (33) of JP-A-2 174 677 (Tonen Corp) Jul. 6, 1990 Abstract.
Koyama, et al., *Journal of Reproductive Immunology*, 19:131–148 (1991).
Biological Abstracts, A. Hasegawa, Abstract No. 91113039 of Acta Obstetrica et Gynaecologica Japonica, 43(2):221–226 (1991).
P. M. Wassarman, "Zona Pellucida Glycoproteins", *Ann. Rev. Biochem*, 1988, 57, pp. 415–442.
A. G. Sacco, "Zona Pellucida", *Am. J. Reproductive Immunology & Microbiology* 1987, 15, pp. 122–130.

Primary Examiner—Christine M. Nucker
Assistant Examiner—Michael Tuscan
Attorney, Agent, or Firm—David G. Conlin; David S. Resnick

[57] ABSTRACT

This invention relates to a DNA sequence comprising at least part of a porcine zona pellucida PZP-4α or -4β gene coding for an amino acid sequence represented by SEQ ID NO: 1 or SEQ ID NO: 2, respectively, in SEQUENCE LISTING.

This invention also relates to an expression system and to expression of said DNA.

In addition, this invention relates to an immunogenic recombinant polypeptide or peptide which comprises at least part of said amino acid sequence and which is obtained by expressing said DNA, and to a contraceptive vaccine for use in human or other animals which comprises said polypeptide or peptide as an active ingredient.

10 Claims, 15 Drawing Sheets

Fig. 8(A)

| Fig. 8(A) |
|---|
| Fig. 8(B) |

```
EcoRI    EcoRV    HpaI       30  HincII                                    60
 AATTC ATG GAT ATC GGT GTT AAC CAA TTG GTC AAC ACT GCT TTC CCA GGT ATT GTC ACG
     G TAC CTA TAG CCA CAA TTG GTT AAC CAG TTG TGA CGA AAG GGT CCA TAA CAG TGC
       Met Asp Ile Gly Val Asn Gln Leu Val Asn Thr Ala Phe Pro Gly Ile Val Thr
   Glu Phe KpnI          120
TGT CAC GAA AAC AGA ATG GTT GTT GAA TTT CCA AGA ATT TTG GGT ACC AAA ATT CAA TAC
ACA GTG CTT TTG TCT TAC CAA CAA CTT AAA GGT TCT TAA AAC CCA TGG TTT TAA GTT ATG
Cys His Glu Asn Arg Met Val Val Glu Phe Pro Arg Ile Leu Gly Thr Lys Ile Gln Tyr StuI       150                                     180
ACT TCT GTT GTT GAT CCA TTA GCC CTT GAA ATG ATG AAC TGT ACT TAC GTT TTG GAC CCA
TGA AGA CAA CAA CTA GGT AAT CCG GAA CTT TAC TAC TTG ACA TGA ATG CAA AAC CTG GGT
Thr Ser Val Val Asp Pro Leu Gly Leu Glu Met Met Asn Cys Thr Tyr Val Leu Asp Pro HindIII          MluI        BstEII          240
                               210
GAA AAC TTG ACT CTT AAG GCT CCA TAC GAA GCT TGT ACT AAA CGC GTT AGA GGT CAC CAC
CTT TTG AAC TGA GAA TTC CGA GGT ATG CTT CGA ACA TGA TTT GCG CAA TCT CCA GTG GTG
Glu Asn Leu Thr Leu Lys Ala Pro Tyr Glu Ala Cys Thr Lys Arg Val Arg Gly His His
```

Fig. 8(B)

```
                                  270                                                     300
CAA ATG ACT ATT AGA TTG ATT GAT GAT AAC GCT GCT TTG AGA CAA GAA GCC TTG ATG TAC
GTT TAC TGA TAA TCT AAC TAA CTA TTG CGA CGA AAC TCT GTT CTT CGG AAC TAC ATG
Gln Met Thr Ile Ile Arg Leu Ile  Asp Asp Asn Ala Ala Leu Arg Gln Glu Ala Leu Met Tyr

NarI      330
CAC ATT TCT TGT CCA GTT ATG GGC GCC GAA GGT CCA GAT CAA CAC TCC GGA TCT ACT ATT
GTG TAA AGA ACA GGT CAA TAC CCG CGG CTT CCA GGT CTA GTT GTG AGG CCT AGA TGA TAA
His Ile Ser Cys Pro Val Met Gly Ala Glu Gly Pro Asp Gln His Ser Gly Ser Thr Ile

390                BamHI  SalI
TGT ATG AAA GAT TTC ATG TCT GTT TCT GAA TGG GGT TGA TAA GGA TCC AGG CAG C
ACA TAC TTT CTA AAG TAC AGA CAA AGA CTT ACC CCA ACT ATT CCT AGG CAG C
Cys Met Lys Asp Phe Met Ser Val Ser Glu Trp Gly STP STP Gly Ser Val Asp
```

Fig. 9
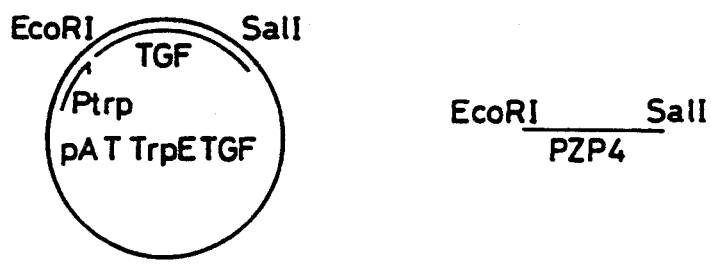
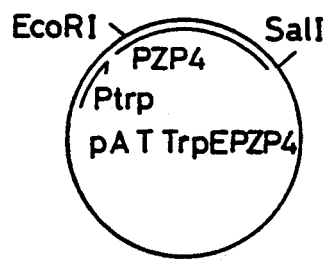
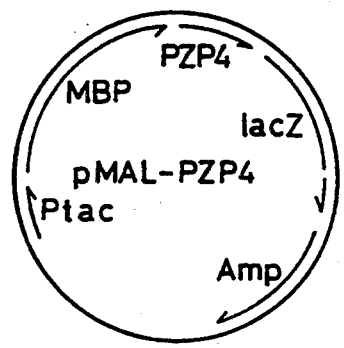

Fig. 10

Culture / Extraction

Rich medium + glucose + ampicillin 800 ml
- + preculture 20 ml
- + IPTG (0.3mM)/0.4 OD
- add 100 μg/ml of ampicillin

↓ culture for 3 hrs

↓ centrifugation (5000 rpm / 20 min)

↓ precipitation

- + lysis buffer (50 ml)

↓ freezing/thawing (-80°C / 30 min → on ice)

↓

Ultrasonication (5 min x 3)

- add NaCl to a concentration of 0.5M (1.16g)

↓ centrifugation (15000 rpm/30 min)

↓ supernatant (crude extract)

Fig. 11

Affinity column chromatography column(amylose resin;1.5g)

↓ wash with 30ml of 0.25% Tween-20-column buffer

↓ apply the crude extract

↓ wash with 30ml of 0.25% Tween-20-coulumn buffer

↓ wash with 50ml of the column buffer

↓ elute with 60ml of elution buffer(column buffer+10mM maltose)

↓ pool fractions collected

↓ dialyze against sterillized water

Enzymatic reaction by Factor Xa protein-containing fractions(1mg/5ml)

| +500 ul of 10x Factor Xa buffer
| +Factor Xa

↓ incubate at room temperature

| 15 hrs

HPLC

Fig. 14(A)

| Fig.14 (A) |
|---|
| Fig.14 (B) |

```
                                              StuI
                                      5'-G G T A G G C C T
                                         C C A T C C G G A
  1                                                  10
I l e G l y V a l A s n G l n L e u V a l A s n T h r A l a
A T C G G C G T T A A T C A A C T C G T T A A T A C A G C A
T A G C C G C A A T T A G T T G A G C A A T T A T G T C G T

```
                                                  100
GlnGluAlaLeuMetTyrHisIleSerCys
CAAGAGGCTCTCATGTATCACATCAGCTGT
GTTCTCCGAGAGTACATAGTGTAGTCGACA

110
ProValMetGlyAlaGluGlyProAspGln
CCTGTTATGGGAGCAGAAGGCCCTGATCAG
GGACAATACCCTCGTCTTCCGGGACTAGTC

120
HisSerGlySerThrIleCysMetLysAsp
CATTCGGGATCCACAATCTGCATGAAAGAT
GTAAGCCCTAGGTGTTAGACGTACTTTCTA
                                        128
PheMetSerValSerGluTrpGly
TTCATGTCTGTAAGTGAATGGGGCTGACTG
AAGTACAGACATTCACTTACCCCGACTGAC

CTTCTCAGCAGGCTACTGCAGGGAAGATAT
GAAGAGTCGTCCGATGACGTCCCTTCTATA
       XbaI
GGTCTAGACAG-3'
CCAGATCTGTC
```

GENES ENCODING PORCINE ZONA PELLUCIDA PROTEIN PZP-4, EXPRESSION THEREOF AND CONTRACEPTIVE VACCINES COMPRISING EXPRESSED (POLY) PEPTIDES

BACKGROUND OF THE INVENTION

1. Field of the Invention

This invention relates to a gene encoding a proteinous component PZP-4 of porcine zona pellucida, and to a contraceptive vaccine antigen prepared by expressing the gene, for use in human or other animals.

2. Prior Art

Unlike the general sterilization such as Pill, IUD, condom, rhythm method, operative sterilization, etc., the sterilization by inoculation of vaccines belongs to an immunological one. It has been suggested that zona pellucida can be used as an antigen for the contraceptive vaccine. When the zona pellucida is therefore inoculated as a vaccine antigen into human or other animals, a specific antibody to the antigen is formed in their bodies, by which fertilization or ovum growth is inhibited to result in contraception.

Among zona pellucidae from various sources, porcine zona pellucida has been mainly studied as a source of such a vaccine antigen. Development of the contraceptive vaccines has been attempted using the whole porcine zona pellucida (PZP-1 of a molecular weight 80 to 90 kDa, PZP-2 of 60 to 65 kDa, PZP-3 of 55 kDa, and PZP-4 of 20 to 25 kDa (Wassarman P. M., "Zona Pellucida Glycoproteins", *Ann. Rev. Biochem.*, 1988, Vol.57, pp.415-420)), or using only the PZP-3 component (Sacco A. G., "Zona Pellucida: Current Status as a Candidate Antigen for Contraceptive Vaccine Development", *American Journal of Reproductive Immunology and Microbiology*, 1987, Vol.15, pp.122-130).

Unfortunately, it is necessary to collect a large quantity of ovaries in order to obtain a sufficient amount of a PZP antigen to prepare a contraceptive vaccine, because a zona pellucida is present only in ovaries. This entails a problem in that an industrially sufficient amount of the antigen cannot be produced. In addition, during purification of zona pellucida other ovarian tissues may be contaminated in a preparation, resulting in an enhanced side effect in animals when the preparation was administered thereto as a vaccine.

It is therefore desirable to prepare a zona pellucida or its components by means of genetic engineering techniques, because a polypeptide useful for a contraceptive vaccine can be obtained in a large scale without depending on materials from living bodies.

An object of the present invention is to provide a genetic engineering process for the production of a zona pellucida PZP-4-related (poly)peptide useful for a contraceptive vaccine.

Another object of the present invention is to provide a contraceptive vaccine which can be prepared in a large scale from a supplier other than living bodies.

SUMMARY OF THE INVENTION

As described in Japanese Patent Application No. 3-82906 filed by the present applicant, we have found that a porcine zona pellucida component, PZP-4, is effective as a contraceptive vaccine. Moreover, we have succeeded in determining the whole base sequence of a gene coding for the PZP-4, as well as the whole amino acid sequence deduced therefrom.

The present invention provides a DNA sequence comprising at least part of a PZP-4α gene coding for an amino acid sequence represented by SEQ ID NO: 1.

The present invention also provides a DNA sequence comprising at least part of a PZP-4β gene coding for an amino acid sequence represented by SEQ ID NO: 2.

In addition, the present invention provides an expression vector capable of expressing and replicating said DNA sequence.

The present invention also provides a host cell transformed with said expression vector.

The present invention further provides an immunogenic recombinant polypeptide or peptide which comprises at least part of said amino acid sequence represented by SEQ ID NOs: 1 or 2, as well as a process for the production of said polypeptide or peptide.

The present invention also provides a contraceptive vaccine comprising said immunogenic recombinant polypeptide or peptide as an active ingredient, as well as a method for contraception.

BRIEF DESCRIPTION OF THE DRAWINGS

FIGS. 8A-8B show a DNA sequence coding for the PZP-4 and capable of expressing in *E. coli* and a deduced amino acid sequence, together with potential restriction sites on the DNA sequence.

FIG. 9 illustrates the construction of an expression vector of this invention, the construction being described in Example 2.

FIG. 10 illustrates a method for culturing a transformant and extracting a recombinant (poly)peptide, the method being described in Example 2.

FIG. 11 illustrates a method for the purification of the recombinant (poly)peptide, the method being described in the Example 2.

Figure 1:
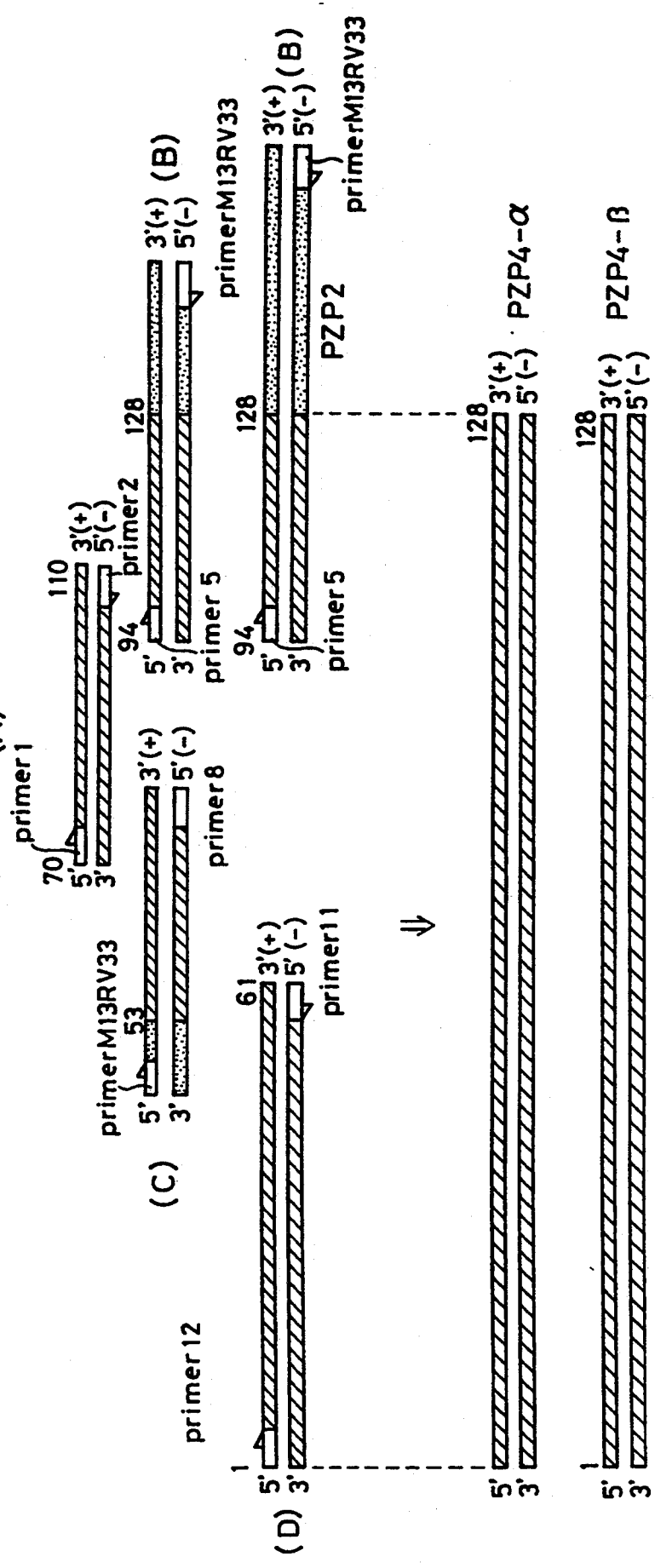
FIG. 1 shows an arrangement of cloned DNA fragments for use in determination of the whole base sequence of PZP-4 gene, together with a strategy for determining the sequence.

directed against PZP-4, wherein the immunoreactive (poly)peptides were stained with NBT and BCIP.

FIGS. 14A–14B show a DNA sequence coding for the PZP-4α and a deduced amino acid sequence, which DNA sequence can be expressed in *E. coli*.

DETAILED DESCRIPTION OF THE INVENTION

As described in detail in the Examples, a base sequence of the PZP-4 gene of the present invention was determined after amplifying a PZP-4 cDNA included in a porcine ovary cDNA library by PCR technique. An amino acid sequence of the PZP-4 was deduced on the basis of the base sequence determined. Thus, the whole amino acid sequences of PZP-4α and PZP-4β were determined in which five amino acids of the C-terminal side are different from each other. Their sequences are shown in SEQ ID NO: 1 and SEQ ID NO: 2, respectively, in SEQUENCE LISTING.

Accordingly, the present invention provides a DNA sequence comprising at least part of a PZP-4α or -4β, gene sequence cording for an amino acid sequence represented by SEQ ID NOs: 1 or 2, respectively. The DNA sequence may be the whole of or part of said PZP-4α or -4β gene sequence.

Particular base sequences of the genes coding for PZP-4α and PZP-4β as determined in the Examples, are shown in SEQ ID NO: 3 and SEQ ID NO: 4, respectively. These sequences and all other sequences based on the degeneracy of codons are also included within the scope of the invention.

The present invention therefore provides a (poly)peptide useable in a contraceptive vaccine, the (poly)peptide comprising at least the immunogenic part of said amino acid sequence of PZP-4α or -4β. The term "immunogenic" as used herein means that the production of an antibody directed against the (poly)peptide can be induced when administering only the (poly)peptide, and that, when the (poly)peptide is administered by binding it to a suitable immunogenic carrier such as albumin, the production of an antibody directed against the (poly)peptide as an epitope is induced. In the aforesaid amino acid sequence of PZP-4, a partial sequence thereof which consists of about 5 or more amino acids may therefore be effective as a vaccine antigen for contraception. However, to avoid such a complex handling that a (poly)peptide is bound to a carrier, the (poly)peptide should preferably have an ability of inducing by itself the production of an antibody thereto, the preferred (poly)peptide consisting of about 10 or more, more preferably about 20 or more amino acids.

Such a (poly)peptide can be synthesized easily by using, for example, a commercially available peptide synthesizer since the amino acid sequence thereof has now been found. If the (poly)peptide is longer and therefore cannot be made by chemical synthesis, it can be obtained by preparing a DNA fragment coding for the (poly)peptide, inserting the fragment into a commercially available expression vector, and then expressing the (poly)peptide in a host containing the vector, such as *E. coli*. The DNA fragment can be synthesized easily by using a commercially available DNA synthesizer if the fragment consists of about 200 or less bases. When the DNA fragment is longer, any region of the amino acid sequence of PZP-4 can be obtained by amplifying the PZP-4 gene by PCR technique using a porcine ovary cDNA library as a template, cloning any region of the PZP-4 gene, and then inserting the resulting DNA fragment into a suitable commercially available expression vector.

As described in the foregoing, a vaccine antigen of the present invention can be produced either by peptide synthesis or by genetic engineering techniques, the latter procedure being preferable when the number of amino acids exceeds 40 because it is difficult to synthesize such a long peptide chemically.

According to the present invention, an immunogenic recombinant polypeptide or peptide, as an active ingredient of the vaccine for contraception, which comprises at least part of an amino acid sequence represented by SEQ ID NO: 1 or SEQ ID NO: 2, can be produced by genetic engineering techniques, that is to say, by constructing an expression vector which contains a region coding for the polypeptide or peptide and can express the region in a suitable host cell such as *E. Coli*; transforming the host cell with the expression vector to isolate a transformant; culturing the transformant in an appropriate medium; and then recovering and purifying the resulting polypeptide or peptide from the culture.

Both the polypeptide or peptide thus obtained and the process for the production thereof are also included within the scope of the present invention.

In the expression vector according to the present invention, a region coding for a (poly)peptide of the invention may comprise any base sequence based on the degeneracy of codons, provided that the sequence encodes the inventive (poly)peptide. However, when *E. coli* is used as a host, it is preferable to use any codon compatible with *E. coli* and to avoid a sequence such as palindrome.

The base sequence coding for an amino acid sequence of PZP-4 is preferably a sequence shown in FIGS. 8A–8B.

A promoter such as tac promoter to improve an efficiency of transcription is present at a site upstream from a (poly)peptide-encoding region of the present invention. The (poly)peptide-encoding region may be located at a site immediately downstream from the promoter, or, as shown in the Examples, it may be located at a site downstream from a region coding for an *E. coli* protein such as *E. coli* maltose-binding protein, TrpE protein or the like. In the latter case, the (poly)peptide of the present invention is produced in the form of fused protein.

An expression vector of the present invention may generally comprise a suitable selection marker such as an antibiotic resistance gene, and a replication origin for initiating a replication of the vector in a host cell. In addition, there may be present a termination codon at a site downstream from a (poly)peptide-encoding region of the present invention. Commercially available vectors useable in *E. coli*, such as pUC9, pBR322 and the like, may be used as a vector.

The expression vector can be constructed by synthesizing the (poly)peptide-encoding region using a conventional technique such as phosphoamidite method, and then cloning the resulting DNA fragment into a known expression vector capable of expressing in *E. coli*. According to one embodiment of the present invention, a PZP-4-encoding region is cloned into an *E. coli* TGF-α expression vector (described in Japanese Patent Application No. 63-28908) or commercially available expression vector (pMAL-c, New England Biolabs). A preferred example of the expression vector is plasmid pMAL-PZP4.

Transformation of a host cell with the inventive expression vector can be carried out in the same way as that with a conventional *E. coli* vector. A preferred example of the transformant is a strain pMAL-PZP4/HB101. *E. coli* strains as transformant can be cultured under suitable conditions commonly used for *E. coli*.

Recovery and purification of a recombinant polypeptide or peptide which was produced by an *E. coli* strain pre-transformed with the expression vector may be effected by collecting organisms by centrifugation, disrupting them by a conventional means such as lysozyme and/or ultrasonic and subsequently extracting, and then subjecting the resulting extract to column chromatography or the like. Conditions for the steps of recovery and purification will be described in detail in the Examples.

It is well known to a person skilled in the art that a (poly)peptide with a certain physiological activity often hold the similar activity, even after addition, deletion or substitution occurred on some amino acids which constitute the (poly)peptide. Therefore, it should be understood that any variant of the above-mentioned PZP-4 amino acid sequence, in which a small number of another amino acids are added to the sequence, a small number of the current amino acids are deleted, or a small number of the current amino acids are substituted by another amino acids, is substantially the same as the PZP-4 amino acid sequence so far as the variant has the similar immunogenicity for contraception, and that the term "amino acid sequence" as used in the specification and the appended claims is intended to include such a variant. The same is also applied to a gene coding for said amino acid sequence.

Accordingly, the present invention also provides an immunogenic recombinant polypeptide or peptide which comprises at least part of an amino acid sequence represented by SEQ ID NO: 1 or SEQ ID NO: 2.

The polypeptide or peptide of the present invention can be formulated into a vaccine for contraception by conventional methods. Accordingly, the present invention further provides a contraceptive vaccine for use in human or other animals, which comprises said polypeptide or peptide as an active ingredient. For example, the contraceptive vaccine may be prepared by suspending the recombinant (poly)peptide in Freund's complete adjuvant at a concentration of from about 10 μg/ml to about 100 μg/ml.

An antibody to the recombinant (poly)peptide in human or other animals is generally formed by inoculating the vaccine into human or other animals several times at intervals of 2 to 4 weeks and at a dose of 10–100 μg of the recombinant (poly)peptide/time, the vaccine being formulated in the form of suspension in Freund's complete adjuvant for the first inoculation and in the form of suspension in Freund's incomplete adjuvant for the second inoculation or hereafter. Timing to be inoculated is not particularly limited.

The present invention further provides a method for the contraception of human or other animals, which comprises administering an effective amount of the vaccine thereto.

The immunological sterilization according to the present invention is regarded as a highly reliable means in comparison with other non-immunological sterilization, because an antibody formed after inoculation of the contraceptive vaccine prevents conception by inhibiting the binding of spermatozoon to ovum or by repressing the growth of follicle in ovary. In addition, since an antibody induced by inoculation of the contraceptive vaccine exhibits cross-reactivity not only with porcine zona pellucida but also with human, rabbit, feline or canine zona pellucida, the vaccine may function effectively as a contraceptive means for human or these animals. In human it has been confirmed that an antibody induced by inoculation of the contraceptive vaccine inhibits fertilization by human spermatozoa. The contraceptive vaccine of the present invention, therefore, can be used effectively as a means to prevent conception in human and to control breeding in other animals such as pets. The present invention has the following advantages:

According to the invention, a gene coding for the PZP-4 useful for a contraceptive vaccine was isolated, a base sequence of the gene was determined, and the whole amino acid sequence of PZP-4 was deduced from the sequence, whereby the PZP-4 can be produced in a large scale by genetic engineering techniques. Various recombinant (poly)peptides of PZP-4, therefore, can be utilized in contraceptive vaccines.

On the basis of the sequence of PZP-4 gene, zona pellucida genes of other animals can also be cloned, whereby more effective vaccines for contraception of animals such as human, dog and cat can also be developed easily.

The present invention will be further illustrated by the following non-limited Examples.

EXAMPLES

Example 1

Cloning of PZP-4 Gene

The whole amino acid sequence of PZP-4 was determined through cloning of the following four DNA fragments:

(A) cloning of a DNA fragment coding for the amino acid sequence between 70 and 110 positions of the PZP-4;

(B) cloning of a 3'-side region of the PZP-4 gene (α: cloning of a DNA fragment coding for the amino acid sequence between 94 and 128 positions of the PZP-4α);

(B) cloning of a 3'-side region of the PZP-4 gene (β: cloning of a DNA fragment coding for the amino acid sequence between 94 and 128 positions of the PZP-4β);

(C) cloning of a 5'-side region of the PZP-4 gene (cloning of a DNA fragment coding for the amino acid sequence between 53 and 86 positions of PZP-4); and (D) cloning of a DNA fragment coding for the amino acid sequence between 1 and 61 positions of the PZP-4.

An arrangement of these fragments and a strategy for determining the whole base sequence of PZP-4 gene are shown in FIG. 1.

Cloning of the DNA fragments were carried out by PCR (i.e. Polymerase Chain Reaction) technique using a PCR reagent kit (GeneAmp DNA Amplification Reagent Kit, Perkin Elmer Cetus) and an automatic PCR apparatus (DNA Thermal Cycler, Perkin Elmer Cetus). The reaction as one cycle was carried out under the conditions of: (1) thermal denaturation step, 94° C. for 1 minute; (2) primer annealing step, 60° C. for 2 minutes; and (3) primer extension step, 72° C. for 3 minutes. The same reactions of 30 cycles were repeated, thereafter the reaction being finally carried out at 72° C. for 7 minutes to complete one round of PCR. DNA primers were synthesized on an automatic DNA synthesizer (Cyclone Plus DNA Synthesizer, Milligen/Biosearch).

Preparation of DNA Template for PCR

Porcine ovaries were ground into powder using a blender in a liquid nitrogen bath, and then extracted using a mRNA extraction kit (Fast Track mRNA isolation kit, Invitrogen) so as to isolate porcine ovary mRNA. The mRNA was converted into a cDNA using a cDNA synthesis kit, which cDNA was thereafter used as a DNA template. A procedure for the cDNA synthesis was varied depending on regions to be cloned. That is, in cloning of a DNA fragment coding for the amino acid sequence between 70 and 110 positions of the PZP-4, a cDNA synthesis kit (oligo dT, Pharmacia) was used to synthesize only a single-stranded cDNA which was used as DNA template (referred to as pig ovary 1st cDNA). In the cloning of 3'-and 5'-side regions of the gene, two cDNA synthesis kits (oligo dT) from Pharmacia and from Promega were used to synthesize double-stranded cDNAs. Thereafter, in accordance with the manual attached to the cDNA synthesis kit of Pharmacia, each of the resulting cDNAs was linked to an EcoRI/NotI adaptor and then inserted into pUC18 vector at EcoRI site. The recombinant vectors were used as DNA templates, which are referred to as pig ovary cDNA-pUC18 Pharmacia and pig ovary cDNA-pUC18 Promega, respectively. In cloning of a DNA fragment coding for the amino acid sequence between 1 and 61 positions of the PZP-4, a cDNA synthesis kit from Amersham was used with the primer 5'-GGTGATGGCCACGCACTC-3' ((−) strand DNA sequence coding for the amino acid between 70 and 77 positions of the PZP-4) to synthesize double-stranded cDNA which was used as a DNA template (referred to as PZP4-cDNA).

Figure 2:
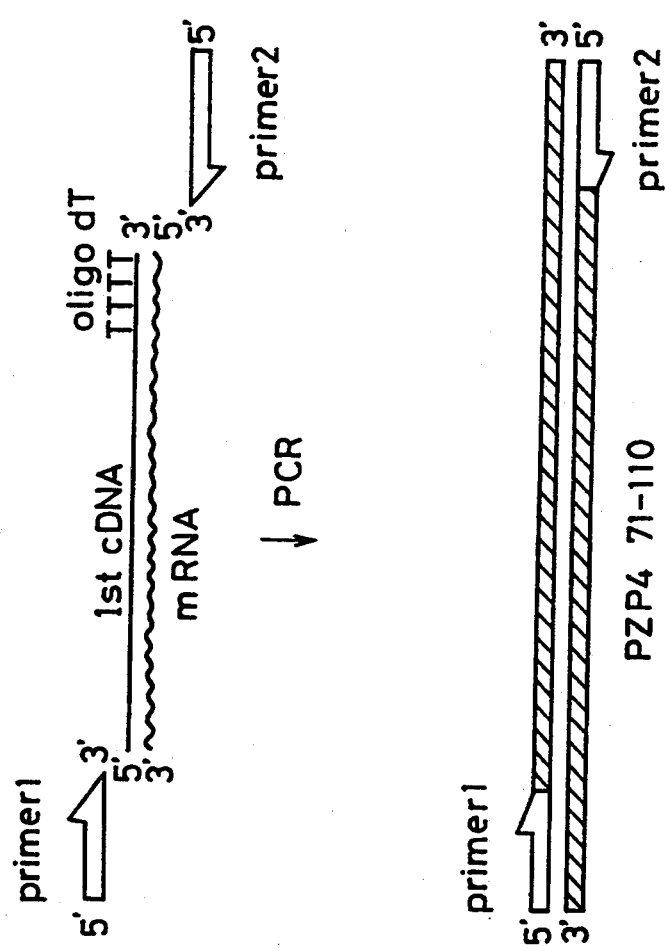
FIG. 2 illustrates a method for the cloning of a DNA fragment coding for the amino acid sequence between 70 and 110 positions of the PZP-4 shown in FIGS. 8A-8B.

(A) Cloning of a DNA Fragment Coding for the Amino Acid Sequence between 70 and 110 Positions of the PZP-4 (FIG. 2)

As disclosed in Japanese Patent Application No. 3-82906 filed by the present applicant, an amino acid sequence 71-110 has been determined as follows:

N-side Arg—Val—Arg—Gly—His—His—Gln—Met—Thr—Ile—Arg—Leu—Ile—
Asp—Asp—Asn—Ala—Ala—Leu—Arg—Gln—Glu—Ala—Leu—Met—Tyr—His—Ile—
Ser—Cys—Pro—Val—Met—Gly—Ala—Glu—Gly—Pro—Asp—Gln C-side.

Based on this amino acid sequence, the following synthetic DNA primers were prepared:

Primer 1: 5'-AAG AGG GTG AGG GGC CA[C,T] CA[C,T] CA[G,A] ATG
           Lys Arg Val Arg Gly His His Gln Met
           AC-3'; and Primer 2: 5'-CTGGTCGGGGCCCTC[G,A]GC[T,C,G,A]CCCAT-3' wherein brackets [ ] indicate a mixture of bases. Primer 1 is a (+) DNA sequence coding for the amino acid sequence between 70 and 79 positions of the PZP-4, and primer 2 is a (−) DNA sequence between 103 and 110 positions of the PZP-4. The primers were prepared by adding Lys to the N-side Arg, because Lys-C treatment has been carried out in the amino acid sequence disclosed in Japanese Patent Application No. 3-82906.

PCR was carried out under the reaction conditions described above, using the above-mentioned pig ovary 1st cDNA as DNA template together with the primers 1 and 2 as primers. Amplified DNAs by PCR technique were confirmed by subjecting a sample to 5% polyacrylamide gel electrophoresis and staining the resulting gel with an ethidium bromide solution. A DNA fragment of about 120 bp was purified from the gel, blunt-ended using a DNA blunt end kit (Takara Shuzo, Japan), and then inserted into pUC119 vector at SmaI site using a DNA ligation kit (Takara Shuzo, Japan). Thereafter, competent E. coli JM109 was transformed with the recombinant pUC119 vector. The transformed cells were cultured on LB plate medium supplemented with 20 µg/ml of X-gal, 5 µg/ml of IPTG and 100 µg/ml of ampicillin, and white colonies grown on the medium was picked up and subjected to a small scale culture. Preparation of plasmid was carried out using a plasmid preparation kit (Hi Purity Plasmid Kit, QUIAGEN). The purified plasmid was alkaline-denatured in the general way used for double-stranded DNA sequencing, after which a DNA sequence was determined by dideoxy method using a DNA sequencing kit (SEQUENASE VERSION 2.07-deaza-dGTP Kit, USB). As the results, the 120 bp DNA fragment (PZP4:70-110) had the following base sequence:

5'-AGAGGGTGAGGGGCCATCATCAAATGACCATCAGACTCATAGATGACAATGCTGCTTT
AAGACAAGAGGCTCTCATGTATCACATCAGCTGTCCTGTTATGGGAGCTGAGGGCCCCGAC
CAG-3'.

Amino acid sequence encoded by this base sequence coincided with the above-mentioned amino acid sequence 70–110 of the PZP-4.

Figure 3:
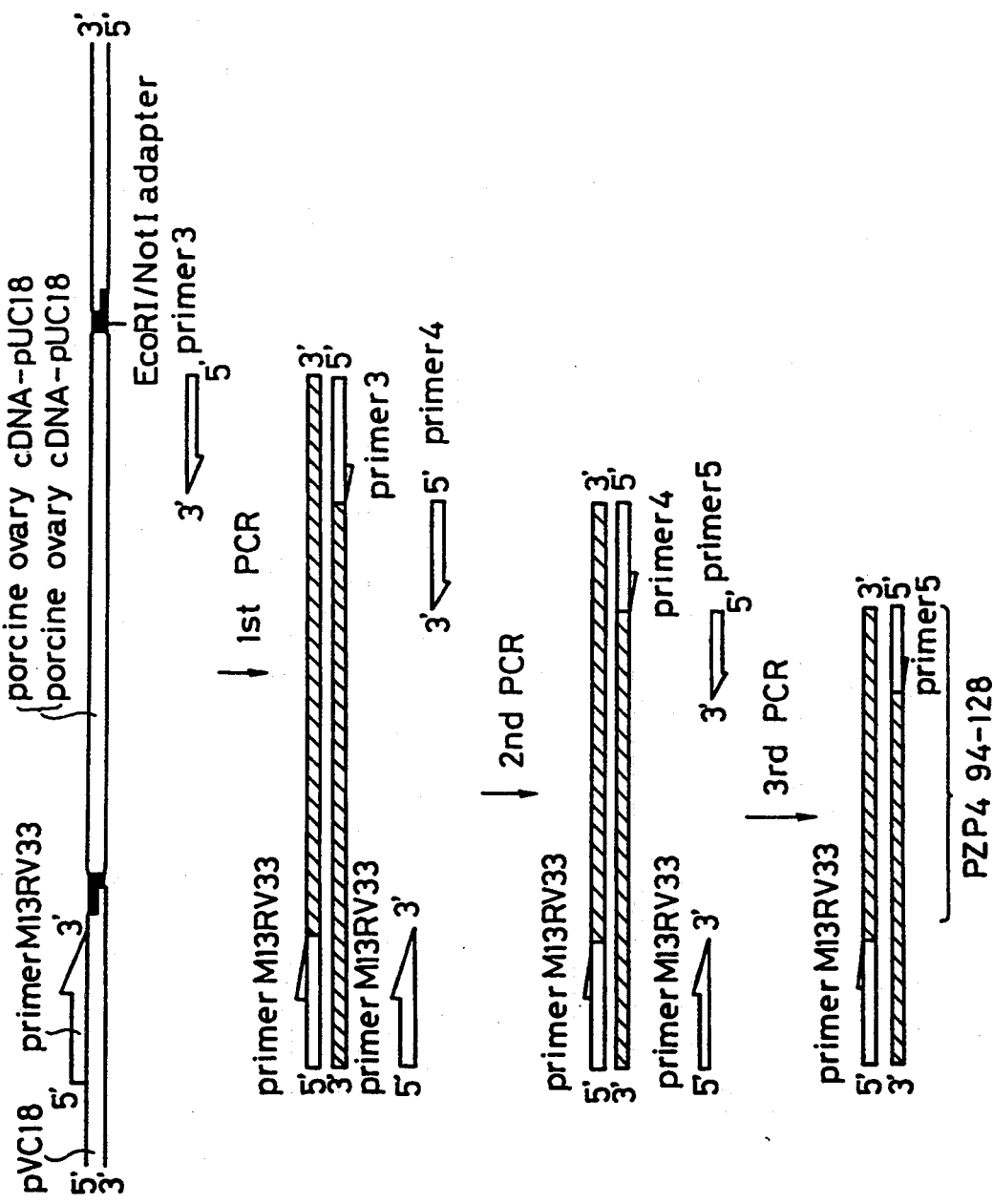
FIG. 3 illustrates a method for the cloning of a DNA fragment coding for the amino acid sequence between 94 and 128 positions of the PZP-4α or -4β shown in SEQ ID NOs: 1 or 2, respectively.

(B) Cloning of a 3'-Side Region of the PZP-4 Gene (Cloning of a DNA Fragment Cording for the Amino Acid Sequence between 94 and 128 positions of the PZP-4α) (FIG. 3)

The following three primers were synthesized based on the DNA sequence coding for the amino acid sequence 71 to 110:

Primer 3: 5'-ATGACCATCAGACTCATAGATGAC-3';
Primer 4: 5'-AATGCTGCTTTAAGACAAGAGGCT-3'; and
Primer 5: 5'-CTCATGTATCACATCAGCTGTCCTGTT-3' wherein primer 3 is a (+) DNA sequence coding for the amino acid sequence between 78 and 85 positions of the PZP-4, primer 4 is a (+) DNA sequence coding for the amino acid sequence between 86 and 93 positions of the same, and primer 5 is a (+) DNA sequence coding for the amino acid sequence between 94 and 102 positions of the same. In addition, the following primer was synthesized based on the sequence of M13 gene in vector pUC18:
Primer M13RV33: 5'-GGATAACAATTT-CACACAGGAAACAGCTATGAC-3'.

Three rounds of PCR were carried out as follows: a first PCR was run using the pig ovary cDNA-pUC18 Pharmacia as DNA template and the primers 3 and M13RV33 as primers; a second PCR was run using a portion of the first PCR product as DNA template and the primers 4 and M13RV33 as primers; and a third PCR was run using a portion of the second PCR product as DNA template and the primers 5 and M13RV33 as primers. Products of the three PCR runs were simultaneously subjected to 5% polyacrylamide gel electrophoresis to examine amplified DNA bands. A DNA band whose size has been reduced by the primer size was purified from the gel. The DNA obtained was cloned and subjected to sequencing in the same manner as in the cloning of a gene coding for the PZP4:70-110. During the cloning, pUC19 was used as a cloning vector and E. coli JM109 as a host. As the results, a DNA fragment coding for the known amino acid sequence (PZP4:94-110) was found in the clone (PZP4:94-128-α), and a base sequence of the DNA fragment (PZP4:94-128-α) coding for the PZP4:94-128-α polypeptide region was determined as follows:

```
5'-TCATGTATCACATCAGCTGTCCTGT-
TATGGGAGCAGAAGGCCCTGATCAG-
CATTCGGG
ATCCACAATCTGCATGAAAGATTT-
CATGTCTGTGAGTGAATGGGGC-3'.
```

(B) Cloning of a 3'-Side Region of the PZP-4 Gene (Cloning of a DNA Fragment Coding for the Amino Acid Sequence between 94 and 128 Positions of the PZP-4β) (FIG. 3)

The sequencing of a 3'-side region of the PZP-4 gene was carried out in the same way as in the cloning of a DNA fragment coding for the amino acid sequence between 94 and 128 positions of the PZP-4α, except that the pig ovary cDNA-pUC18 Promega was used as a template of the first PCR; E. coli DH5α as a host for transformation; and pUC119 as a vector. As the results, a DNA fragment coding for the known amino acid sequence (PZP4:94-110) was found in the clone (PZP4:94-128-β), and a base sequence of the DNA fragment (PZP4:94-128-β) coding for the PZP4:94-128-β polypeptide region was determined as follows:

```
5'-CTCATGTATCACATCAGCTGTCCTGT-
TATGGGAGCAGAAGGCCCTGATCAG-
CATTCGG
GATCCACAATCTGCATGAAAGATTT-
CATGTCTTTTACCTTTAACTTT-3'.
```

Figure 4:
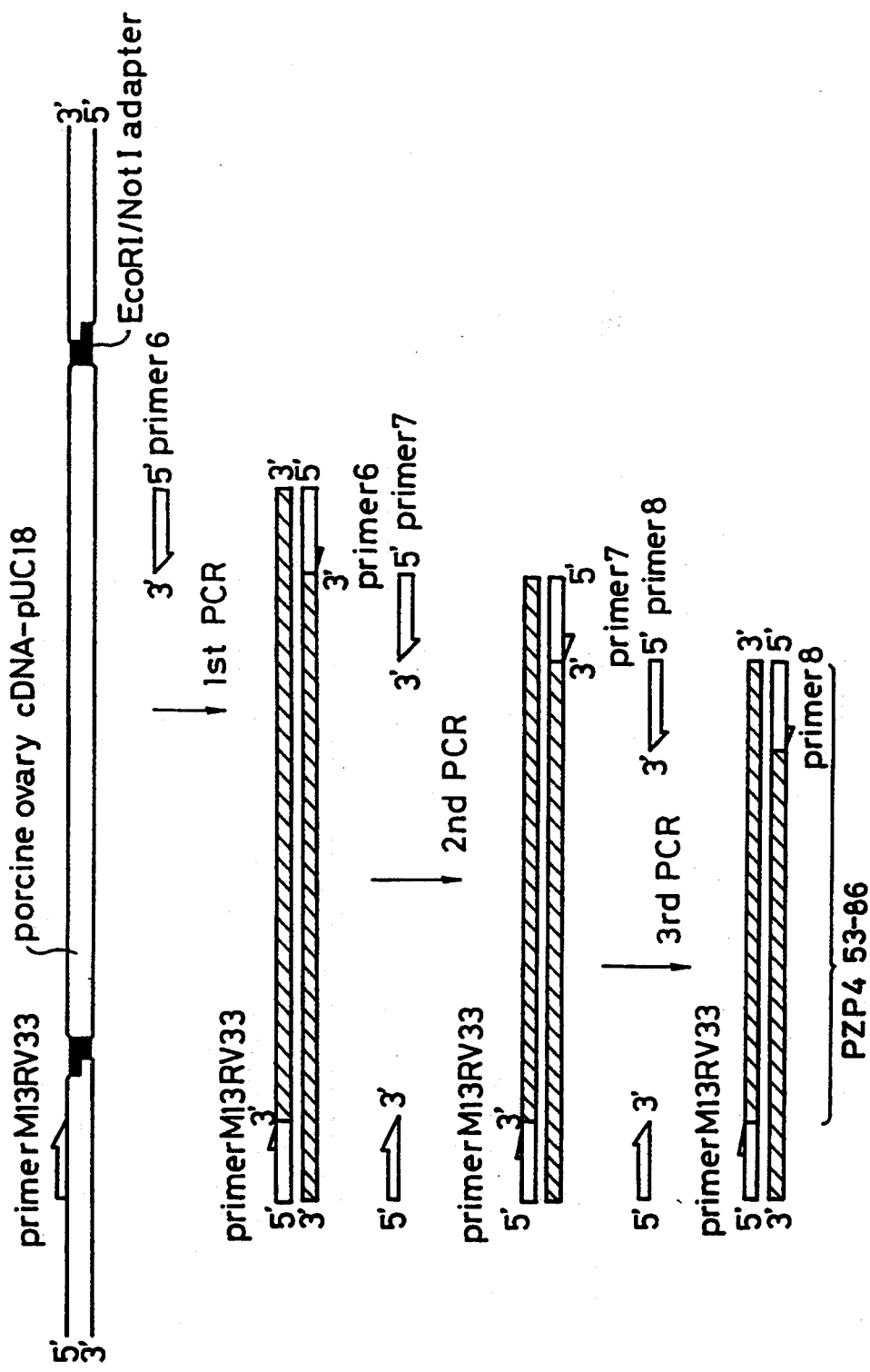
FIG. 4 illustrates a method for the cloning of a DNA fragment coding for the amino acid sequence between 53 and 86 positions of the PZP-4 shown in FIGS. 8A-8B.

(C) Cloning of a 5'-Side Region of the PZP-4 Gene (Cloning of a DNA Fragment Coding for the Amino Acid Sequence between 53 and 86 positions of the PZP-4) (FIG. 4)

The following primers were synthesized based on the base sequence coding for the PZP4:70-110 polypeptide region:
Primer 6: 5'-CATAACAGGACAGCTGATGT-GATACAT-3';
Primer 7: 5'-GAGAGCCTCTTGTCTTAAAG-CAGC-3'; and
Primer 8: 5'-ATTGTCATCTATGAGTCT-GATGGTCAT-3'
wherein primer 6 is a (−) strand DNA sequence coding for the amino acid sequence between 95 and 103 positions of the PZP-4, primer 7 is a (−) strand DNA sequence coding for the amino acid sequence between 87 and 94 positions of the same, and primer 8 is a (−) strand DNA sequence coding for the amino acid sequence between 78 and 86 positions of the same. Three rounds of PCR was carried out as follows:

a first PCR was run using the pig ovary cDNA-pUC18 Pharmacia as DNA template and the primers 6 and M13RV33 as primers; a second PCR was run using a portion of the first PCR product as DNA template and the primers 7 and M13RV33 as primers; and a third PCR was run using a portion of the second PCR product as DNA template and the primers 8 and M13RV33 as primers.

In the same way as in the cloning of a gene coding for the PZP4:94-128 polypeptide region, products of the three PCR runs were subjected to electrophoresis, a DNA band whose size was reduced by the primer size was purified from the gel, the DNA obtained was cloned, and then a base sequence of the clone (PZP4:53-86) was determined. During the cloning, pUC19 and E. coli DH5α) strain were used as a cloning vector and as a host, respectively. As the results, a gene coding for the known amino acid sequence (PZP4:70-86) was found in the clone (PZP4:53-86), and a base sequence of the gene (PZP4:53-86) coding for the PZP4:53-86 polypeptide region was determined as follows:

```
5'-ACACAGGAAACAGCTATGACCATGATTCGCGGCCGCGTTCTGGACCCAGAAAACCTCA
CCCTGAAGGCCCCATATGAAGCCTGTACCAAAAGAGTGCGTGGCCATCACCAAATGACCAT
CAGACTCATAGATGACAA-3'.
```

Figure 5:
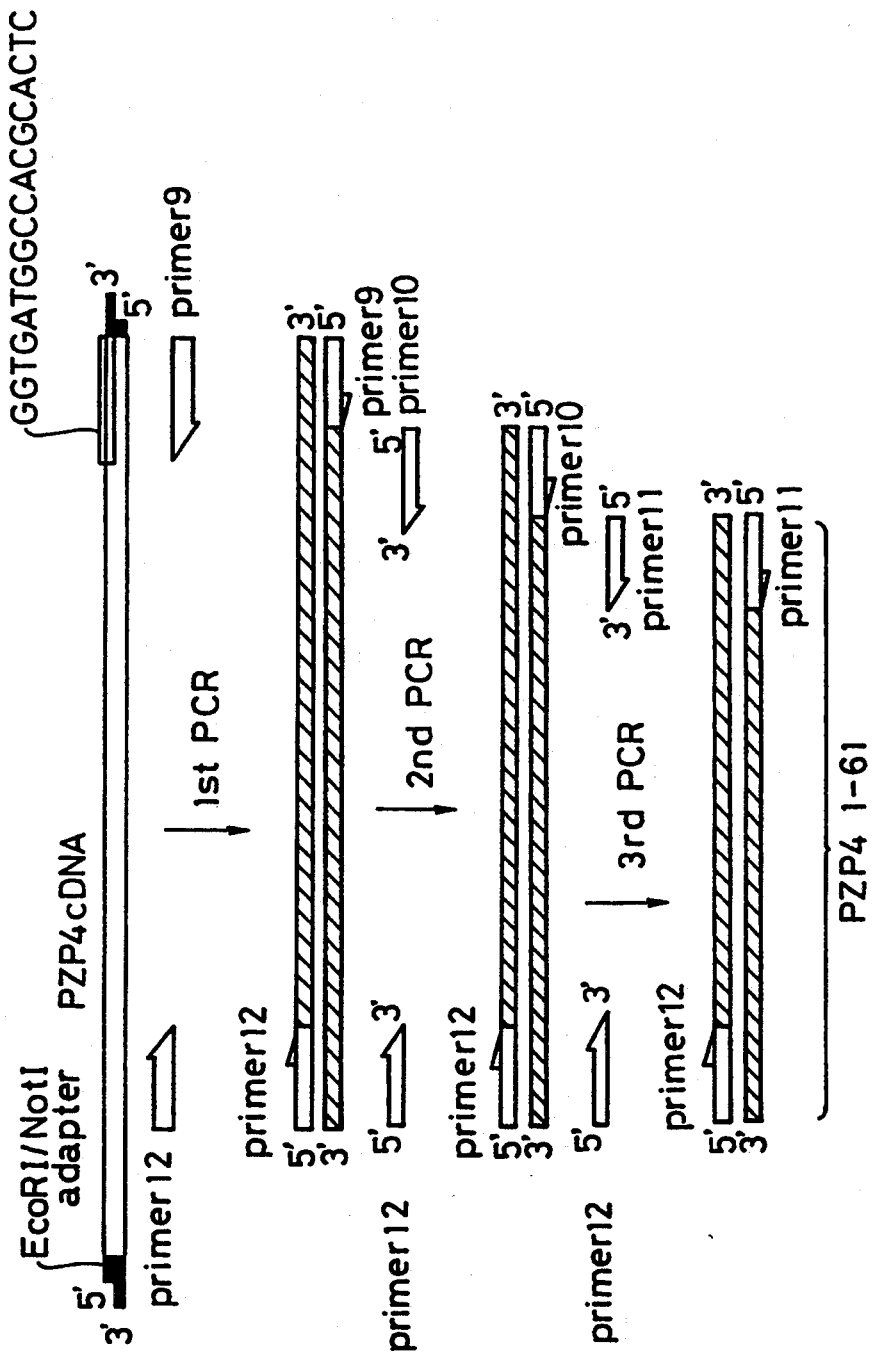
FIG. 5 illustrates a method for the cloning of a DNA fragment coding for the amino acid sequence between 1 and 61 positions of the PZP-4 shown in FIGS. 8A-8B.

(D) Cloning of a DNA Fragment Coding for the Amino Acid Sequence between 1 and 61 Positions of the PZP-4 (FIG. 5)

PZP-4 was separated and purified from porcine ovaries by a modification (Japanese Patent Application No. 3-82906) of O'Farrell's method, and its N-terminal amino acid sequence (corresponding to 1 to 21 positions of the PZP-4) was determined as follows using an amino acid sequencer (477A; Applied Biosystems):

N-side Ile—Gly—Val—Asn—Gln—Leu—Val—Asn—Thr—Ala—Phe—Pro—Gly—Ile—Val—Thr—( )-His—Glu—Asn—Arg C-side.

The following synthetic DNA primer was prepared based on this sequence:
Primer 12: 5'-ATCGGCGTTAATCAACTCGT-TAATAC [C,A]GC[G,T,C,A]TT[C,T]CC-3'.

Primer 12 is a (+) strand DNA sequence coding for the amino acid sequence between 1 and 12 positions of the PZP-4.

In addition, the following three primers were synthesized based on the base sequence coding for the PZP4:53-86 polypeptide region:
Primer 9: 5'-TTGGTGATGGCCACGCACTCTTTT-3';
Primer 10: 5'-GGTACAGGCTTCATATGGGGCCTT-3'; and
Primer 11: 5'-CAGGGTGAGGTTTTCTGGGTCCAG-3'
wherein primer 9 is a (−) strand DNA sequence coding for the amino acid sequence between 70 and 77 positions of the PZP-4, primer 10 is a (−) strand DNA sequence coding for the amino acid sequence between 62 and 69 positions of the PZP-4, and primer 11 is a (−) strand DNA sequence coding for the amino acid sequence between 54 and 61 positions of the PZP-4.

Three rounds of PCR were carried as follows: a first PCR was run using the PZP4-cDNA as DNA template and the primers 9 and 12 as primers, a second PCR was run using a portion of the first PCR product as DNA template and the primers 10 and 12 as primers, and a third PCR was run using a portion of the second PCR product as DNA template and the primers 11 and 12 as primers.

In the same way as in the cloning of a gene coding for the PZP4:94-128 polypeptide region, products of the three PCR runs were subjected to electrophoresis, a DNA band whose size was reduced by the primer size was purified from the gel, the DNA obtained was cloned, and then a base sequence of the clone was determined. During the cloning, pUC119 and $E.$ $coli$ DH5α were used as a cloning vector and as a host to be transformed, respectively. As the results, a DNA fragment coding for the amino acid sequence (PZP4:1-21) previously determined was found in the clone (PZP4:1-61). The following is the determined base sequence of the DNA fragment (PZP4:1-61) coding for the amino acid sequence of the PZP4:1-61 polypeptide region:

5'-ATCGGCGTTAATCAACTCGTTAATACAGCATTTCCAGGTATTGTCACTTGCACATGAA
AATAGAATGGTAGTGGAATTTCCAAGAATTCTTGGCACTAAGATACAGTACACCTCTGTGG
TGGACCCTCTTGGTCTTGAAATGATGAACTGTACCTATGTTCTGGACCCAGAAAACCTCAC
C-3'.

By linking together five base sequences of the cloned PZP-4 DNA fragments, the whole base sequence of the PZP-4 gene and an amino acid sequence encoded by the gene were determined (FIGS. 8A–8B).

Figure 6:
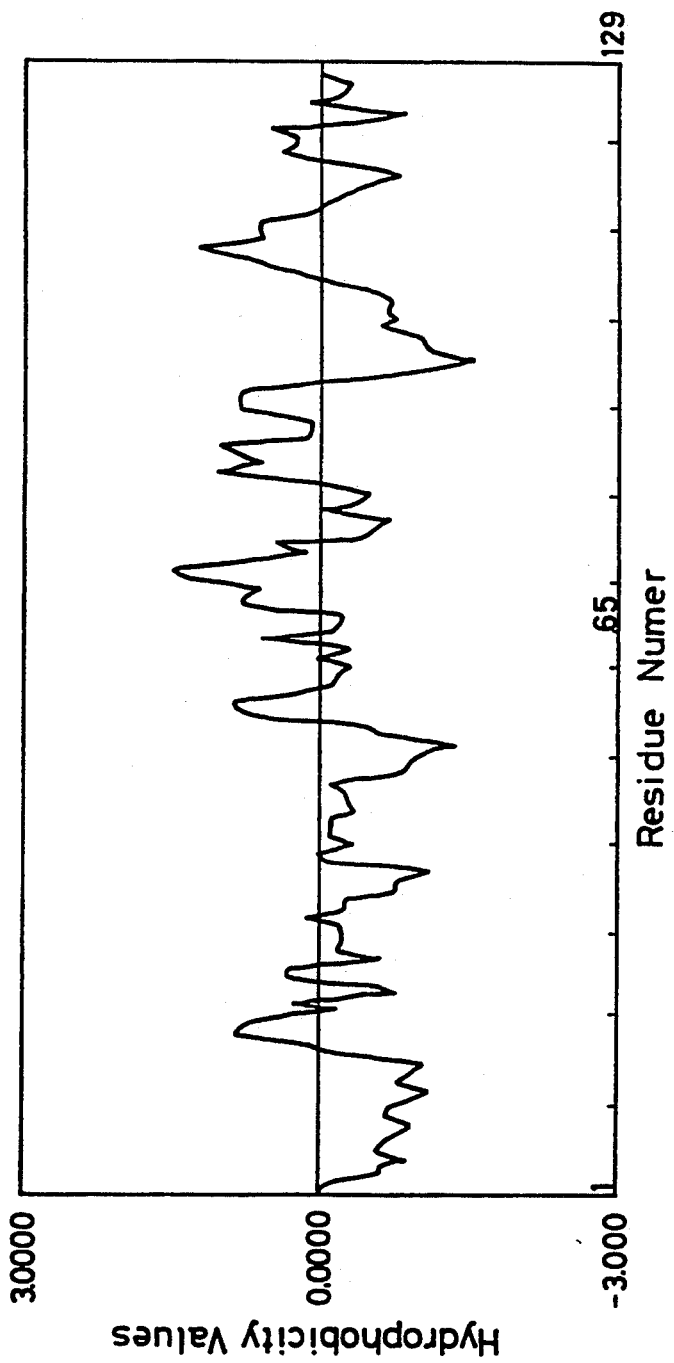
FIG. 6 is a graph illustrating the relationship of hydrophobicity value vs residue number in PZP-4α as determined by Hoop-Woods' method.
Figure 7:
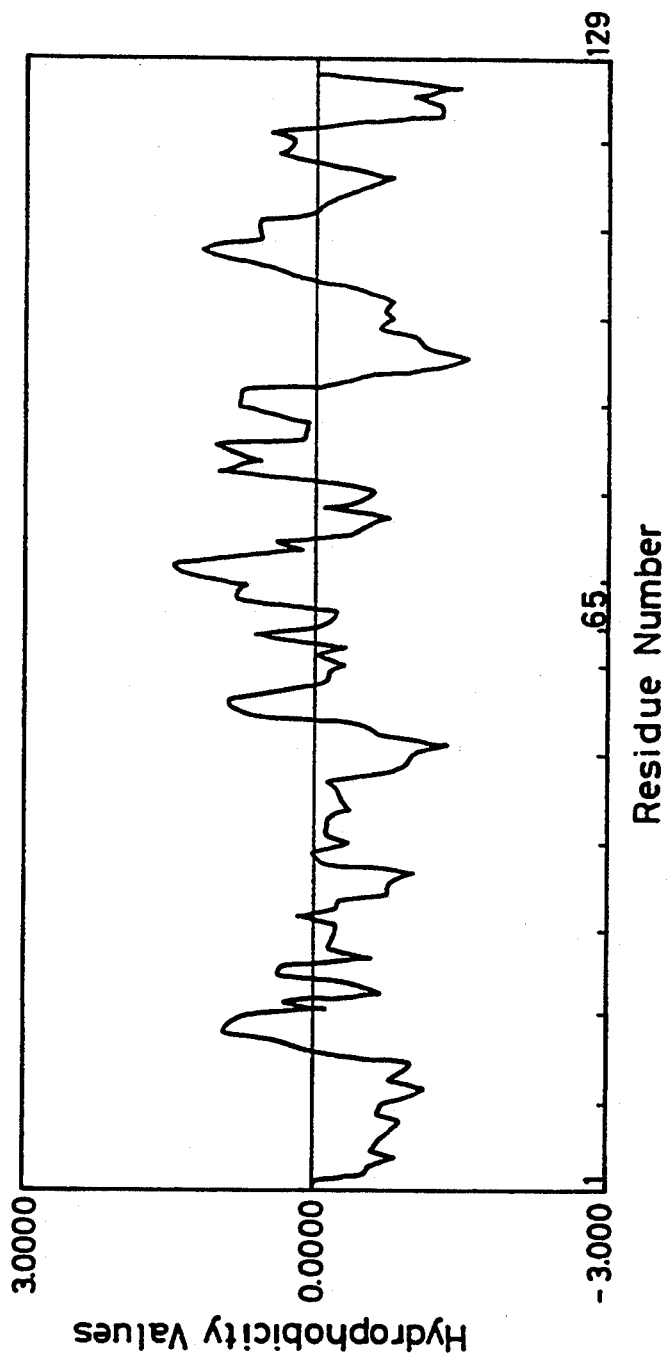
FIG. 7 is a graph illustrating the relationship of hydrophobicity value vs residue number in PZP-4β as determined by Hoop-Woods' method.

Hydrophilic and hydrophobic regions of PZP-4α and PZP-4β were estimated by Hoop-Woods' method. The results are shown in FIGS. 6 and 7, respectively. In general, antigen epitopes are believed to locate at a region where hydrophilic amino acid residues are gathered and closely contacted with water. In the PZP-4, hydrophilic regions are presumed to be present at 19, 25, 56, 70, 85, 90, 110, 120 positions, etc. in the amino acid sequence of the PZP-4, thus indicating possible existence of antigen epitopes on the regions.

Example 2

(1) Construction of cloning vector:

As shown in FIG. 8, DNA fragments of the PZP-4 gene, which have been designed in such a manner that each of the fragments consists of about 60 base pairs, were synthesized by phosphoamidite method. The synthesized fragments were purified by reverse phase chromatography and then treated with T4 ligase so as to obtain a PZP-4 gene.

The thus-obtained gene whose 5'- and 3'-ends have EcoRI and SalI recognition sites, respectively, was inserted into a cloning vector pUC9 which has been digested with EcoRI and SalI. $E.$ $coli$ JM107 strain was transformed with the recombinant vector and then cultured overnight on L-medium in the presence of 40 µg/ml of ampicillin, IPTG and X-gal to obtain a candidate strain.

After extracting plasmid DNA from the candidate strain, a base sequence of the inserted gene was examined by Sanger's method to confirm that the gene has the sequence designed. A strain carrying the PZP-4 gene-containing cloning vector was named pUC-PZP4/JM107.

(2) Construction of expression vector (FIG. 9):

Plasmid DNA prepared from the pUC-PZP4/JM107 was digested with EcoRI and SalI and extracted to obtain a PZP-4 gene fragment of about 420 base pairs. Using T4 ligase, the fragment was then ligated with a large fragment of the expression vector pAT-TrpE-TGF-α which has been digested with EcoRI and SalI. $E.$ $coli$ HB101 strain was transformed with the ligated product and then cultured overnight on L-medium in the presence of 400 µg/ml of ampicillin to obtain a candidate strain, pAT-TrpE-PZP4/HB101.

Plasmid DNA prepared from the strain pAT-TrpE-PZP4/HB101 was digested with EcoRI and SalI and extracted to obtain a PZP-4 gene fragment of about 410 base pairs. Using T4 ligase, the fragment was then ligated with a large fragment of the expression vector pMAL-c (New England Biolabs) which has been digested with StuI and SalI. $E.$ $coli$ HB101 strain was transformed with the ligated product and cultured overnight on L-medium in the presence of 400 µg/ml of ampicillin to obtain a candidate strain named pMAL-PZP4/HB101. These procedures are summarized in FIG. 9.

(3) Purification of expressed protein (FIGS. 10 and 11):

The strain pMAL-PZP4/HB101 containing the constructed expression vector was cultured so as to examine the expression of a recombinant protein. The strain pMAL-PZP4/HB101 was cultured overnight in 100 ml of L-medium supplemented with 40 µg/ml of ampicillin. Thereafter, 20 ml of the culture was inoculated into 1 L of Rich medium (10 g of tryptone, 5 g of enzyme extracts, and 5 g of sodium chloride in 1 L) cotaining 2 g of glucose and cultured at 37° C. When absorbance at 600 nm reached 0.4, IPTG (isopropyl-1-thio-β-D-thiogalactoside) was added to a final concentration of 0.3 mM, after which the culturing were continued for further 3 hours, and 2 g of organisms were collected by centrifugation. The organisms were then suspended in a lysis buffer (10 mM phosphate, 30 mM sodium chloride, 0.25% of Tween 20, 10 mM β-ME, 10 mM EDTA and 10 mM EGTA), subjected to freezing-thawing, and then disrupted by ultrasonication. Soluble fraction was collected by centrifugation and subjected to affinity column chromatography on amylose resin equilibrated with the buffer consisting of 10 mM sodium phosphate, 0.5M sodium chloride, 1 ml of azide, 10 mM β-ME and 1 mM EGTA. Eluates containing the desired product were pooled and dialyzed against water, and a maltose-binding protein as a fused protein was digested with a restriction protease Factor Xa in a buffer solution (20 mM Tris-HCl, 100 mM sodium chloride, 2 mM calcium chloride and 1 mM azide). Thereafter, the resulting reaction mixture was subjected to reverse phase HPLC to recover and purify the desired PZP-4 protein. The HPLC was carried out under the conditions of: column, ODS 120T (7.8 mm-I.D.×30 cm-L, TOSOH CORP., Japan); elution solutions, aqueous 0.1% TFA solution (solution A) and 60% acetonitrile/solution A (solution B) with linear gradient (30 min) of solution B from 0 to 80%; flow rate, 3 ml/min; and detection, 220 nm. As the results, two peaks appeared, a later peak being of the PZP-4 protein which was subsequently identified to be homogeneous by SDS-polyacrylamide gel electrophoresis. The procedures employed are shown in FIGS. 10 and 11.

Example 3

Determination of Immunogenicity of Recombinant PZP-4 Protein

We tested, by western blotting, whether or not the recombinant PZP-4 antigen protein prepared in Example 2 has the same immunogenicity as the natural type PZP-4 antigen protein.

Figure 12:
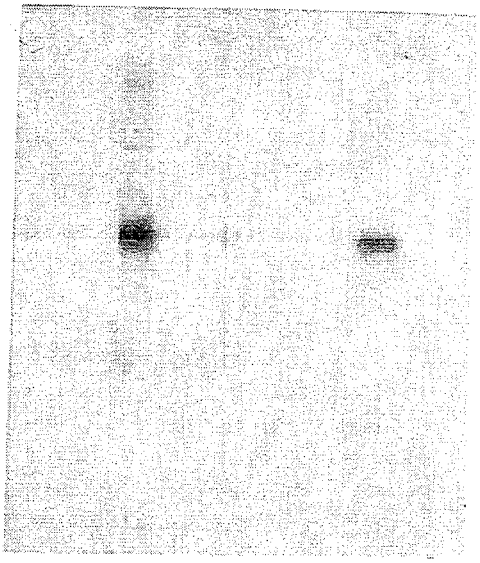
FIG. 12 is an electrophoretic pattern showing the reactivity of a recombinant (poly)peptide obtained in Example 2 with antibodies (Anti-PZP4 and MoAb 5H4) directed against PZP-4, wherein the immunoreactive (poly)peptides were stained with NBT and BCIP.
Figure 13:
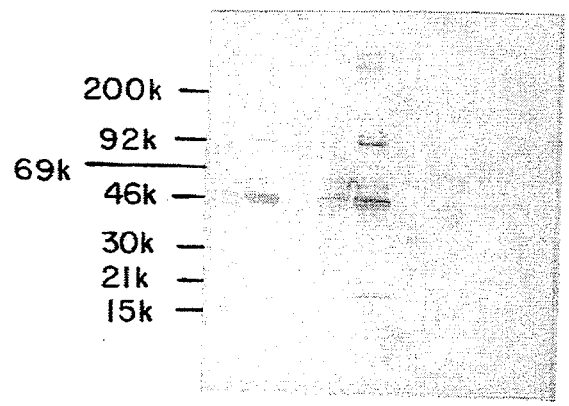
FIG. 13 is an electrophoretic pattern showing the reactivity of a recombinant (poly)peptide obtained in Example 2 with antibodies (Anti-PZP4 and MoAb 5H4)

An *E. coli* strain capable of expressing the recombinant PZP-4 antigen protein were cultured and the resulting organisms were collected in the same manner as in Example 2. A portion of the organisms were solubilized in a sample buffer (reducing conditions) of Lammli's method and applied to 18% polyacrylamide gel to perform SDS-electrophoresis in the conventional way. After completion of the electrophoresis, proteins were conventionally transferred from the acrylamide gel to a nitrocellulose filter using a commercially available electrotransfer apparatus. The filter was then blocked by soaking it in a 2% skim milk-TBST (10 mM Tris-HCl, 0.14M NaCl, 0.1% Tween 20, pH 7.5), and then soaked in the solution containing a monoclonal antibody 5H4 (MoAb5H4 disclosed in Japanese Patent Application No. 2-253031) or anti-PZP4 serum (diluted to 1:1,000) prepared from natural type PZP-4, these antibodies having been previously subjected to an absorption treatment by adding to the antibody-containing solution the same *E. coli* strain in which protein antigens other than the PZP-4 protein are expressed. The antigen-anibody reactions were carried out overnight at 4° C. As negative controls, both a monoclonal antibody 2F10 (MoAb2F10), which is of the same IgG class or subclass as MoAb5H4, directed against the other antigen and a normal mouse serum (NMS) were used in the same manner. After the reaction, the filter was washed three times by soaking it in TBST and then reacted with a commercially available anti-mouse IgG antibody labeled with alkaline phosphatase. Thereafter, the filter was washed three times with TBST and then color-developed using NBT and BCIP. As shown in FIGS. 12 and 13, color development was found only in MoAb5H4 and anti-PZP4 serum. These results show that the amino acid sequence of the present invention coincides with the sequence of a protein generally called PZP-4, and that the recombinant PZP-4 protein artificially produced in *E. coli* has the same immunogenicity as that of the natural type PZP-4 protein.

Thus, according to the present invention, not only natural zona pellucida but also the recombinant type PZP-4 proteins produced by genetic engineering techniques in *E. coli* as claimed in the appended claims can be used as the antigen source for contraceptive vaccines.

Example 4

A DNA fragment having a sequence shown in FIGS. 14A–14B was prepared in the same manner as in Example 2 to obtain PZP-4α gene. Since the PZP-4α gene has StuI and XbaI recognition sites on its 5'- and 3'-ends, respectively, the gene was digested with StuI and XbaI and then, using T4 ligase, inserted into the expression vector pMAL-c which has been digested with the same restriction endonucleases. *E. coli* JM109 was transformed with the resulting vector to obtain a candidate PZP-4α expression strain in the same manner as in Example 2. Thereafter, the candidate strain was cultured and its capacity of expressing the PZP-4α gene was positively confirmed in the same manner as in Example 3.

---

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH:128
        ( B ) TYPE:amino acid
        ( C ) TOPOLOGY:linear ( i i ) MOLECULE TYPE: peptide ( x i ) SEQUENCE DESCRIPTION:SEQ ID NO:1:

```
Ile  Gly  Val  Asn  Gln  Leu  Val  Asn  Thr  Ala  Phe  Pro  Gly  Ile  Val  Thr
 1                  5                       10                          15

Cys  His  Glu  Asn  Arg  Met  Val  Val  Glu  Phe  Pro  Arg  Ile  Leu  Gly  Thr
20                       25                       30

Lys  Ile  Gln  Tyr  Thr  Ser  Val  Val  Asp  Pro  Leu  Gly  Leu  Glu  Met  Met
```

```
                35                          40                          45

Asn   Cys   Thr   Tyr   Val   Leu   Asp   Pro   Glu   Asn   Leu   Thr   Leu   Lys   Ala   Pro
50                          55                          60

Tyr   Glu   Ala   Cys   Thr   Lys   Arg   Val   Arg   Gly   His   His   Gln   Met   Thr   Ile
65                          70                          75                          80

Arg   Leu   Ile   Asp   Asp   Asn   Ala   Ala   Leu   Arg   Gln   Glu   Ala   Leu   Met   Tyr
85                          90                          95

His   Ile   Ser   Cys   Pro   Val   Met   Gly   Ala   Glu   Gly   Pro   Asp   Gln   His   Ser
100                         105                         110

Gly   Ser   Thr   Ile   Cys   Met   Lys   Asp   Phe   Met   Ser   Val   Ser   Glu   Trp   Gly
115                         120                         125
```

( 2 ) INFORMATION FOR SEQ ID NO:2:

( i ) SEQUENCE CHARACTERISTICS:
        ( A ) LENGTH:128
        ( B ) TYPE:amino acid
        ( C ) TOPOLOGY:linear ( i i ) MOLECULE TYPE:peptide ( x i ) SEQUENCE DESCRIPTION:SEQ ID NO:2:

```
Ile   Gly   Val   Asn   Gln   Leu   Val   Asn   Thr   Ala   Phe   Pro   Gly   Ile   Val   Thr   Cys
1                           5                           10                          15

His   Glu   Asn   Arg   Met   Val   Val   Glu   Phe   Pro   Arg   Ile   Leu   Gly   Thr   Lys   Ile
20                          25                          30

Gln   Tyr   Thr   Ser   Val   Val   Asp   Pro   Leu   Gly   Leu   Glu   Met   Met   Asn   Cys   Thr
35                          40                          45                          50

Tyr   Val   Leu   Asp   Pro   Glu   Asn   Leu   Thr   Leu   Lys   Ala   Pro   Tyr   Glu   Ala   Cys
55                          60                          65

Thr   Lys   Arg   Val   Arg   Gly   His   His   Gln   Met   Thr   Ile   Arg   Leu   Ile   Asp   Asp
70                          75                          80                          85

Asn   Ala   Ala   Leu   Arg   Gln   Glu   Ala   Leu   Met   Tyr   His   Ile   Ser   Cys   Pro   Val
90                          95                          100

Met   Gly   Ala   Glu   Gly   Pro   Asp   Gln   His   Ser   Gly   Ser   Thr   Ile   Cys   Met   Lys
105                         110                         115

Asp   Phe   Met   Ser   Phe   Thr   Phe   Asn   Phe
120                         125
```

( 2 ) INFORMATION FOR SEQ ID NO:3:

( i ) SEQUENCE CHARACTERISTICS:
        ( A ) LENGTH:384 base pairs
        ( B ) TYPE:nucleic acid
        ( C ) STRANDEDNESS:double
        ( D ) TOPOLOGY:linear ( i i ) MOLECULE TYPE:cDNA to mRNA ( x i ) SEQUENCE DESCRIPTION:SEQ ID NO:3:

```
ATCGGCGTTA   ATCAACTCGT   TAATACAGCA   TTTCCAGGTA   TTGTCACTTG   CCATGAAAAT      60
AGAATGGTAG   TGGAATTTCC   AAGAATTCTT   GGCACTAAGA   TACAGTACAC   CTCTGTGGTG     120
GACCCTCTTG   GTCTTGAAAT   GATGAACTGT   ACTTATGTTC   TGGACCCAGA   AAACCTCACC     180
CTGAAGGCCC   CATATGAAGC   CTGTACCAAA   AGAGTGCGTG   GCCATCACCA   AATGACCATC     240
AGACTCATAG   ATGACAATGC   TGCTTTAAGA   CAAGAGGCTC   TCATGTATCA   CATCAGCTGT     300
CCTGTTATGG   GAGCAGAAGG   CCCTGATCAG   CATTCGGGAT   CCACAATCTG   CATGAAAGAT     360
TTCATGTCTG   TAAGTGAATG   GGGC                                                  384
```

( 2 ) INFORMATION FOR SEQ ID NO:4:

( i ) SEQUENCE CHARACTERISTICS:
   ( A ) LENGTH:384 base pairs
   ( B ) TYPE:nucleic acid
   ( C ) STRANDEDNESS:double
   ( D ) TOPOLOGY:linear ( i i ) MOLECULE TYPE:cDNA to mRNA ( x i ) SEQUENCE DESCRIPTION:SEQ ID NO:4:

```
ATCGGCGTTA  ATCAACTCGT  TAATACAGCA  TTTCCAGGTA  TTGTCACTTG  CCATGAAAAT    60

AGAATGGTAG  TGGAATTTCC  AAGAATTCTT  GGCACTAAGA  TACAGTACAC  CTCTGTGGTG   120

GACCCTCTTG  GTCTTGAAAT  GATGAACTGT  ACTTATGTTC  TGGACCCAGA  AAACCTCACC   180

CTGAAGGCCC  CATATGAAGC  CTGTACCAAA  AGAGTGCGTG  GCCATCACCA  AATGACCATC   240

AGACTCATAG  ATGACAATGC  TGCTTTAAGA  CAAGAGGCTC  TCATGTATCA  CATCAGCTGT   300

CCTGTTATGG  GAGCAGAAGG  CCCTGATCAG  CATTCGGGAT  CCACAATCTG  CATGAAAGAT   360

TTCATGTCTT  TTACCTTTAA  CTTT                                             384
```

We claim:
1. DNA encoding PZP-4α having SEQ ID NO: 3.
2. DNA encoding PZP-4β having SEQ ID NO: 4.
3. An expression vector containing the DNA according to claim 1.
4. An expression vector containing the DNA according to claim 2.
5. Plasmid pMAL-PZP4.
6. A host cell transformed with the expression vector according to claim 3.
7. A host cell transformed with the expression vector according to claim 4.
8. A host cell pMAL-PZP4/HB101 strain transformed with the plasmid pMAL-PZP4 of claim 5.
9. A process for the production of a recombinant PZP-4α polypeptide having an amino acid sequence shown in SEQ ID NO: 1, which comprises the steps of:

(a) constructing an expression vector which contains the DNA according to claim 1,
(b) introducing said expression vector into a host cell to obtain a transformant;
(c) culturing said transformant in a suitable medium to express said DNA; and
(d) recovering and purifying the expressed polypeptide.

10. A process for the production of a recombinant PZP-4β polypeptide having an amino acid sequence shown in SEQ ID NO: 2, which comprises the steps of:

(a) constructing an expression vector which contains the DNA according to claim 2,
(b) introducing said expression vector into a host cell to obtain a transformant;
(c) culturing said transformant in a suitable medium to express said DNA; and
(d) recovering and purifying the expressed polypeptide.

* * * * *